United States Patent
Havel et al.

(10) Patent No.: US 7,286,873 B2
(45) Date of Patent: Oct. 23, 2007

(54) METHOD OF OPTIMIZING MECHANICAL HEART RATE DURING DELIVERY OF COUPLED OR PAIRED PACING

(75) Inventors: William J. Havel, Maple Grove, MN (US); Paul G. Krause, St. Louis Park, MN (US); Karen J. Kleckner, New Brighton, MN (US); D. Curtis Deno, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 247 days.

(21) Appl. No.: 11/096,388

(22) Filed: Mar. 31, 2005

(65) Prior Publication Data

US 2006/0224197 A1    Oct. 5, 2006

(51) Int. Cl.
*A61N 1/362* (2006.01)
(52) U.S. Cl. .......................................................... 607/9
(58) Field of Classification Search ...................... 607/9
See application file for complete search history.

(56) References Cited

U.S. PATENT DOCUMENTS

| | | | | |
|---|---|---|---|---|
| 5,861,007 A * | 1/1999 | Hess et al. | ...................... | 607/9 |
| 6,772,005 B2 * | 8/2004 | Casavant et al. | ............... | 607/4 |
| 2004/0049235 A1 * | 3/2004 | Deno et al. | ..................... | 607/9 |
| 2005/0101998 A1 * | 5/2005 | Kleckner et al. | ............... | 607/4 |

\* cited by examiner

*Primary Examiner*—Carl Layno
*Assistant Examiner*—Yun Haeng Lee
(74) *Attorney, Agent, or Firm*—Paul H. McDowall; Steve Bauer

(57) ABSTRACT

A method of operating a cardiac pacing device that optimizes the mechanical heart rate using coordinated potentiation therapy while maximizing the opportunity for intrinsic AV conduction to occur. The method may include adjusting the timing of extra stimulus intervals during coupled or paired pacing to promote AV conduction and to effect changes in rate according to certain embodiments of the invention. Other embodiments may include adjusting the atrial pacing rate to achieve a desired target rate consistent with AV conduction. A mode switch to a dual-chamber pacing mode may be provided according to certain embodiments of the invention to ensure a ventricular rate that meets or exceeds a minimum mechanical rate.

14 Claims, 6 Drawing Sheets

| State # | AV Conduction | As? (Sinus Rate > Apace Rate) | Ap? (Apace Rate >= Sinus Rate) | At or Below Target Rate? | At or Below Min Rate? | Transition (Action Taken) |
|---|---|---|---|---|---|---|
| 1 | Present | Yes | No | No | No | None |
| 2 | Absent | Yes | No | No | No | ↑ $A_{sense} - A_{CP}$ |
| 3 | Present | No | Yes | Yes | No | ↓ $A_{pace} - A_{pace}$ w/ probing |
| 4 | Present | Yes | No | Yes | No | ↓ $A_{pace} - A_{pace}$ |
| 5a | Absent | No | Yes | Yes | No | ↓ $A_{pace} - A_{CP}$; |
| 5b | Absent | No | Yes | Yes | No | ↑ $A_{pace} - A_{pace}$ |
| 6 | Absent | Yes | No | Yes | No | ↑ $A_{sense} - A_{CP}$ |
| 7 | Present | No | Yes | Yes | Yes | $A_{pace} - A_{pace}$ = Min Rate; ↓ $A_{pace} - A_{pace}$ w/ probing |
| 8 | Absent (V-pacing) | No | Yes | Yes | Yes | $A_{pace} - A_{pace}$ = Min Rate, $V_{pace} - V_{pace}$ = Min Rate, with periodic inhibition of V-pacing; |

| State # | AV Conduction | As? (Sinus Rate > Apace Rate) | Ap? (Apace Rate >= Sinus Rate) | At or Below Target Rate? | At or Below Min Rate? | Transition (Action Taken) |
|---|---|---|---|---|---|---|
| 1 | Present | Yes | No | No | No | None |
| 2 | Absent | Yes | No | No | No | ↑ $A_{sense} - A_{CP}$ |
| 3 | Present | No | Yes | Yes | No | ↓ $A_{pace} - A_{pace}$ w/ probing |
| 4 | Present | Yes | No | Yes | No | ↓ $A_{pace} - A_{pace}$ |
| 5a | Absent | No | Yes | Yes | No | ↓ $A_{pace} - A_{CP}$; |
| 5b | Absent | No | Yes | Yes | No | ↑ $A_{pace} - A_{pace}$ |
| 6 | Absent | Yes | No | Yes | No | ↑ $A_{sense} - A_{CP}$ |
| 7 | Present | No | Yes | Yes | Yes | $A_{pace} - A_{pace}$ = Min Rate; ↓ $A_{pace} - A_{pace}$ w/ probing |
| 8 | Absent (V-pacing) | No | Yes | Yes | Yes | $A_{pace} - A_{pace}$ = Min Rate, $V_{pace} - V_{pace}$ = Min Rate, with periodic inhibition of V-pacing; |

FIG. 6

METHOD OF OPTIMIZING MECHANICAL HEART RATE DURING DELIVERY OF COUPLED OR PAIRED PACING

FIELD

Embodiments of the invention relate generally to cardiac pacing devices, and more particularly to a method and apparatus for optimizing the mechanical heart rate during cardiac potentiation therapy (CPT).

BACKGROUND

Cardiac pacing devices, such as cardiac pacemakers, implantable cardioverter defibrillators (ICDs), and cardiac resynchronization therapy (CRT) devices are available to provide pacing therapy to a heart. Early cardiac pacemakers were asynchronous, single-chamber devices that stimulated a ventricle of the heart at a fixed rate, independent of the patient's underlying cardiac rhythm or metabolic demand. Although such pacemakers, typified by U.S. Pat. No. 3,057,356 to Greatbatch, provided a ventricular pacing rate sufficient to sustain life, this pacing mode often competed with native ventricular rhythms.

Subsequently, demand pacemakers (VVI) were developed. This type of pacemaker provide pacing pulses only when spontaneous ventricular activity is absent. U.S. Pat. No. 3,478,746 to Greatbatch demonstrates an example of such a pacemaker. This form of pacemaker provides a ventricular sense amplifier for detecting ventricular depolarizations. A ventricular sensed event resets the pacemaker's ventricular escape interval (V-V) timer. The ventricular sensed event also cancels or inhibits the scheduled ventricular stimulus and thus avoids competition with the native ventricular rhythm.

Atrial synchronized pacemakers (VAT) were developed almost simultaneously with VVI demand pacemakers. This type of pacemaker paces the ventricle in response to a detected atrial rate. The VAT pacemaker, as typified by U.S. Pat. No. 3,253,596 to Keller, provides an atrial sense amplifier for detecting atrial depolarizations. An atrial sensed event starts the pacemaker's A-V delay timer. When the A-V delay timer times out, a ventricular stimulus is provided. Conceptually, such a pacemaker can be considered as a prosthetic conduction pathway that simulates the natural A-V conduction pathways of the heart. One drawback to this form of pacing is the possibility of competing with ectopic ventricular activity. An ectopic ventricular beat (PVC) may be detected in the atrium (i.e., by far-field sensing of a PVC, for example) and classified as an atrial sensed event. In such cases, the pacemaker may begin an AV interval, resulting in the generation of a ventricular stimulus a short time after the ventricular depolarization. Although such a result may have little effect when the A-V delay is short, it is possible to deliver the pacing stimulus into the vulnerable period of the ventricular depolarization response, and thereby possibly initiate a ventricular arrhythmia.

Continued development of pacemakers was marked by the invention of the AV sequential pacemaker (DVI), as disclosed in U.S. Pat. No. 3,595,242 issued to Berkovits. This form of pacemaker can provide stimulation pulses in both the atrium and the ventricle, while providing sensing only in the ventricle. In the DVI mode pacemaker, a ventricular sense event starts a V-A escape interval followed by an A-V interval. The pacemaker delivers an atrial stimulus at the end of the V-A interval and, at the end of the A-V interval, the pacemaker delivers a ventricular stimulus. If a ventricular sense event occurs during the V-A or A-V time intervals, the pacemaker will resynchronize to the ventricular sense event and inhibit the delivery of the scheduled ventricular stimulus.

The DDI mode pacemaker described by U.S. Pat. No. 3,747,604 to Berkovits further includes an atrial sense amplifier to inhibit the atrial stimulus when an atrial sense event occurs during the V-A interval.

However, the atrial sense event does not start an A-V interval; such timing may make this device suitable in patients where atrial competition should be avoided.

The atrial-synchronized ventricular-inhibited or VDD mode pacemaker, as disclosed in U.S. Pat. No. 3,648,707 issued to Greatbatch has mechanisms for sensing in the atrium and ventricle while providing stimulating pulses only in the ventricle. In operation, the VDD pacemaker starts an A-V interval on detected atrial activity and provides a ventricular stimulus if one does not occur within the A-V delay. A ventricular sensed event inhibits the scheduled ventricular stimulus and resets the pacemaker's V-V timer.

The dual sense, dual pace DDD mode pacemakers, have been described in U.S. Pat. No. 4,312,355 issued to Funke. The DDD mode pacemaker, as described by Funke, has had broad applications. This type of pacemaker has sense amplifiers for detecting atrial and ventricular events, as well as output pulse circuitry for stimulating both the atrium and the ventricle. Pacemakers operating in the DDD mode provide timing circuitry to initiate an A-V delay upon the occurrence of an atrial event, whether sensed or paced. If, during the A-V delay period, no spontaneous ventricular event is sensed, the pacemaker will produce a ventricular stimulus at the conclusion of the A-V delay. If, during the V-A interval, no spontaneous atrial event is sensed, the pacemaker provides an atrial stimulus at the conclusion of the V-A interval.

In the DDD pacemaker mode, in the absence of spontaneous P-waves and R-waves, the heart will be stimulated at fixed A-A and V-V intervals with a programmable AV delay. However, if the ventricle depolarizes spontaneously, the A-V delay is truncated and the observed A-A and V-V intervals may vary according to whether "atrial-based" or "ventricular-based" timing (or some modification thereof) is employed. For example, ventricular-based timing attempts to maintain a constant V-V interval such that spontaneous depolarization of the ventricle during the A-V delay may cause the A-A time to be truncated. Alternatively, atrial-based timing attempts to maintain constant A-A intervals such that spontaneous depolarization of the ventricle during the A-V delay may result in a longer V-V interval.

The dual chamber pacemaker modalities, DVI, VAT, VDD and DDD, attempt to restore A-V synchrony and thus improve cardiac output by ensuring the hemodynamic contribution of the atrial chambers within the pacing regimen. The latter three modes may also synchronize the pacing rate to the patient's native atrial or sinus rate and thus may provide an increased pacing rate in response to bodily activity, thereby increasing cardiac output.

More recently, other pacemakers, which increase cardiac output in response to exercise, have been proposed. They include pacemakers that rely upon the sensing of physical activity via an activity sensor or accelerometer, changes in blood pH, respiratory rate, or QT interval. These data are used to alter the pacemaker's escape intervals, and hence the pacing rate.

An example of an activity responsive pacemaker is described in U.S. Pat. No. 4,428,378, issued to Anderson et al., and incorporated by reference herein. The pacemaker disclosed in that patent monitors the physical activity of the patient and increases the pacing rate in response to an increase in patient physical activity.

U.S. Pat. No. 4,890,617 issued to Markowitz et al., incorporated herein by reference, describes a dual chamber activity responsive pacemaker that senses and paces in both the atrium and the ventricle. The pacing rate is determined by the sensed activity of the patient, the programmed lower rate, and the patient's atrial or sinus rate.

U.S. Pat. No. 4,932,046, entitled "Dual Chamber Rate Responsive Pacemaker," assigned to Medtronic, Inc. of Minneapolis, Minn., which is herein incorporated by reference in its entirety, describes a dual chamber rate responsive pacemaker. The pacemaker operates in an atrial-synchronized modality when the sensed atrial rate is present (i.e., above a sensor-determined rate), and paces at the sensor-determined rate when the sensed atrial rate is absent or below the sensor-determined rate.

DDD pacemakers are often implanted in patients with Sick Sinus Syndrome (SSS), a term that covers a large array of sinus node disease states. Such patients often have intact AV conduction and, if the pacemaker's AV interval is not properly programmed, the pacemaker will deliver an unneeded and undesirable ventricular pacing pulse. Many patients who receive DDD pacemakers (or dual-chamber ICDs with DDD pacing capability) are unnecessarily paced in the ventricle. There appears to be reluctance in the medical community against implanting a DDD device and programming it to the AAI/R mode in patients with sick sinus syndrome (SSS) and intact AV conduction; this reluctance may be due to concerns with transient AV block, for example. Moreover, when programmed to the DDD mode, the AV intervals in these pacemakers may be left at their factory-programmed state, that is, with shorter durations more suitable to third degree AV block patients. As a result, ventricular pacing frequently occurs at the termination of these AV intervals, with little or no possibility of spontaneous ventricular activity occurring.

There is growing medical evidence that inappropriate ventricular pacing may impact hemodynamics and may not be beneficial when allowed to continue for an extended period of time. It has been known in the art as early as 1925 that ventricular pacing results in asynchronous delayed activation of the ventricular tissue and, thereby, produces compromised hemodynamics in mammals. More recently, canine studies have shown that right ventricular apical (RVA) pacing causes a negative "inotropic effect" and a >30% reduction in cardiac efficiency. In addition, long term RVA pacing has been shown to lead to permanent changes including myofibrillar cellular disarray, myocardial perfusion defects, and structural abnormalities. Each of these may further contribute to deterioration of ventricular function.

Various cardiac pacing devices have attempted to address this problem by implementing algorithms that automatically adapt the AV interval duration to preferentially allow AV conduction when present.

In U.S. Pat. No. 5,861,007, issued to Hess, et al, a Search AV operation is described in which the pacemaker continuously monitors for the presence or absence of an intrinsic R-wave after both sensed and paced P-waves. The programmed AV interval may be extended by a programmable "hysteresis" interval to promote ventricular conduction. The extension of the AV interval, however, may be limited in duration due to the interaction with the post-ventricular atrial refractory period (PVARP) at higher rates. This is because the AV interval and the immediately following PVARP together form a Total Atrial Refractory Period (TARP) during which no atrial activity can be sensed (or tracked). Thus, the TARP sets a limit on the maximum rate (the "Upper Rate") at which the DDD mode can track atrial sensed events. To maintain unimpeded upper rate operation, Search AV may work in conjunction with Auto-PVARP (shortening of the PVARP with increasing rates) to maintain atrial sensing and tracking up to the programmed upper rate limit, thereby postponing a 2:1 block operation as long as possible. Since there is a limit to the shortening of the PVARP in this operation, it may become necessary to shorten the AV interval after the PVARP reaches its minimum value. Consequently, many patients (>30%) with intact AV conduction are ventricularly paced to a significant degree (>50%) despite having Search AV programmed on.

Other approaches to the problem are presented in U.S. Pat. No. 5,318,594 issued to Limousin, et al., and in U.S. Pat. No. 6,122,546 issued to Sholder, et al. Limousin describes a DDD Automatic Mode Switch (AMS) pacemaker that operates in a "Special AAI" mode as long as R-wave sensing occurs within a ventricular surveillance window that is calculated based on the history of the measured PR interval. If an R-wave is not sensed within this window, the pacing operation switches to the DDD mode. After 100 consecutive paced ventricular events, the pacemaker attempts to switch back to the Special AAI mode. Sholder implements a form of AV/PV hysteresis. This operation encourages intrinsic conduction by extending the AV interval by a predetermined period beyond the programmed duration. As indicated above, this operation may be restricted to avoid interaction with upper rate tracking.

AV extension algorithms present unique challenges in dual chamber ICDs due to the added requirements of tachyarrhythmia detection. For example, to adequately detect a ventricular tachycardia, the AV delay must be restricted so that the tachycardia detection interval falls within the VA interval at all times. Failure to do so comes at the expense of tachyarrhythmia detection sensitivity. An alternative means to address this issue is by means of a temporary mode change for a programmed period of time following the delivery of a shock. Unfortunately, while this may protect against transient post-shock AV block, it does so at the expense of beat-to-beat monitoring. Consequently, many electrophysiologists do not program the AAI/R mode on a permanent basis to avoid persistent ventricular pacing.

"Ideoventricular kick," first described by Schlant in 1966, (Circulation, 1966; 23 & 24 (Suppl. III): 209) results from improved coherence of the ventricular contraction during normal activation. This hemodynamic benefit is lost during ventricular pacing. In an earlier study of the atrial contribution to ventricular filling (Kosowski B, et al., Re-evaluation of the atrial contribution to ventricular filling: Study showing his-bundle pacing, Am J Cardiol, 1968; 21 518-24), it was demonstrated that ventricular function was better during normal ventricular activation independent of the PR interval. Similarly, a later study (Rosenqvist M, et al., Relative importance of activation sequence compared to atrioventricular filling synchrony in left ventricular function, Am J Cardiol, 1991; 67(2): 148-56) showed that AAI pacing was superior to either VVI or DDD pacing.

Aside from the hemodynamic benefits mentioned above, it may be that normal ventricular activation has a role in preventing tachyarrhythmias. In a study of 77 ICD patients with a mean follow-up of 18.7 months (Roelke M, et al. Ventricular pacing induced ventricular tachycardia in patients with implantable cardioverter defibrillators. PACE, 1995; 18(3): 486-91), appropriately timed ventricular pacing preceded tachyarrhythmia onset in 8.3% of the episodes in five patients. A further study (Belk P, et al. Does ventricular pacing predispose to ventricular tachycardia? Abstract. PACE, April, 2000) demonstrates that high rate ventricular pacing renders patients more susceptible to the induction of ventricular tachycardia compared to high rate atrial pacing with normal ventricular activation.

More recently, the "Dual Chamber and VVI Implantable Defibrillator" (DAVID) Trial concluded that intrinsic conduction may be more desirable than RV apical pacing, and that patients with indications for implantable defibrillators and no indication for pacing should not be paced in the dual chamber pacing mode. Cardiac Electrophysiology Rev. 2003 December, 7(4):468-72.

These studies, combined with the growing body of evidence showing the detrimental effects of long-term ventricular pacing, has led to more deliberate efforts by clinicians to allow for normal ventricular activation when programming dual chamber bradycardia devices. Still, due to the interactions imposed by PVARP and upper rate timing, mode switching, and tachyarrhythmia detection, their best intentions are often thwarted.

In U.S. Pat. No. 6,772,005 to Casavant, et al., herein incorporated by reference in its entirety, an ADI/R mode is implemented using an intelligent pacing system to continually monitor ventricular response. This pacing mode seeks to ensure AV conduction whenever possible so as to gain all the benefits of cardiac contractile properties resulting from native R-waves. In the event where AV conduction is blocked, the pacing mode is switched to a DDD/R mode to ensure a paced R-wave. Thereafter, subsequent to a completed interval of a p-wave, ADI/R pacing resumes to monitor ventricular response.

Techniques for further enhancing cardiac contractile properties include the use of post-extra systolic potentiation (PESP), described by Burnes, et al., in U.S. Published Pat. App. No. 2004/0220631. Post-extra systolic potentiation (PESP) is a property of cardiac myocytes that results in enhanced mechanical function of the heart on the beats following an extra systolic stimulus delivered early after either an intrinsic or pacing-induced systole. An extra stimulus delivered after an intrinsic systole is referred to as coupled (or triggered) pacing, and an extra stimulus delivered after a pacing-induced systole is referred to as paired pacing. The magnitude of the enhanced mechanical function is strongly dependent on the timing of the extra systole relative to the preceding intrinsic or paced systole. When correctly timed, an extra systolic stimulation pulse causes an electrical depolarization of the heart, but the attendant mechanical contraction is absent or substantially weakened. The contractility of the subsequent cardiac cycles, referred to as the post-extra systolic beats, is increased as described in detail in commonly assigned U.S. Pat. No. 5,213,098 issued to Bennett et al., incorporated herein by reference in its entirety.

As noted, the degree of mechanical augmentation on post-extra systolic beats depends on the time interval between a primary systole and the subsequent extra systole, referred to herein as the "extra stimulus interval" (ESI). If the ESI is too long, the PESP effects are not achieved because a normal mechanical contraction takes place in response to the extra systolic stimulus. As the ESI is shortened, a maximal effect is reached when the ESI is slightly longer than the myocardial refractory period. An electrical depolarization occurs without a mechanical contraction or with a substantially weakened contraction. When the ESI becomes too short, the stimulus falls within the absolute refractory period and no depolarization occurs. The use of an appropriately timed PESP extra stimulus in the atrium may be used to effect a slowing of the rate of intrinsic atrial contractions due to resetting of the sinus node. A PESP extra stimulus in the ventricle may occasionally prevent an atrial depolarization from conducting to the ventricles.

As indicated in the above-referenced '098 patent, one potential risk associated with delivering extra systolic stimulation pulses to achieve PESP is the potential for arrhythmia induction. If the extra systolic pulse is delivered to cardiac cells during the vulnerable period, the risk of inducing tachycardia or fibrillation in arrhythmia-prone patients may be high. The vulnerable period encompasses the repolarization phase of the action potential, also referred to herein as the "recovery phase," and a period immediately following it.

What is needed, therefore, is a method of providing cardiac pacing therapy at an appropriate rate that includes the mechanical augmentation benefits of PESP, while maximizing the opportunity for intrinsic AV conduction.

BRIEF SUMMARY

Certain embodiments of the invention provide a method of operating a cardiac pacing device using coupled and paired pacing to maximize the opportunity for intrinsic AV conduction to occur.

Certain embodiments of the invention provide a method of operating a cardiac pacing device to optimize the mechanical heart rate during coupled and paired pacing.

Certain embodiments of the invention provide a method of operating a cardiac pacing device in an atrial-based mode to optimize the mechanical heart rate during coupled and paired pacing and to maximize the opportunity for intrinsic AV conduction to occur, while providing the ability to switch to a dual-chamber mode to provide pacing at a minimum mechanical rate.

BRIEF DESCRIPTION OF THE DRAWINGS

FIG. 6 is a table of the responses provided in accordance with an embodiment of the invention.

DETAILED DESCRIPTION OF THE ILLUSTRATED EMBODIMENTS

Figure 1:
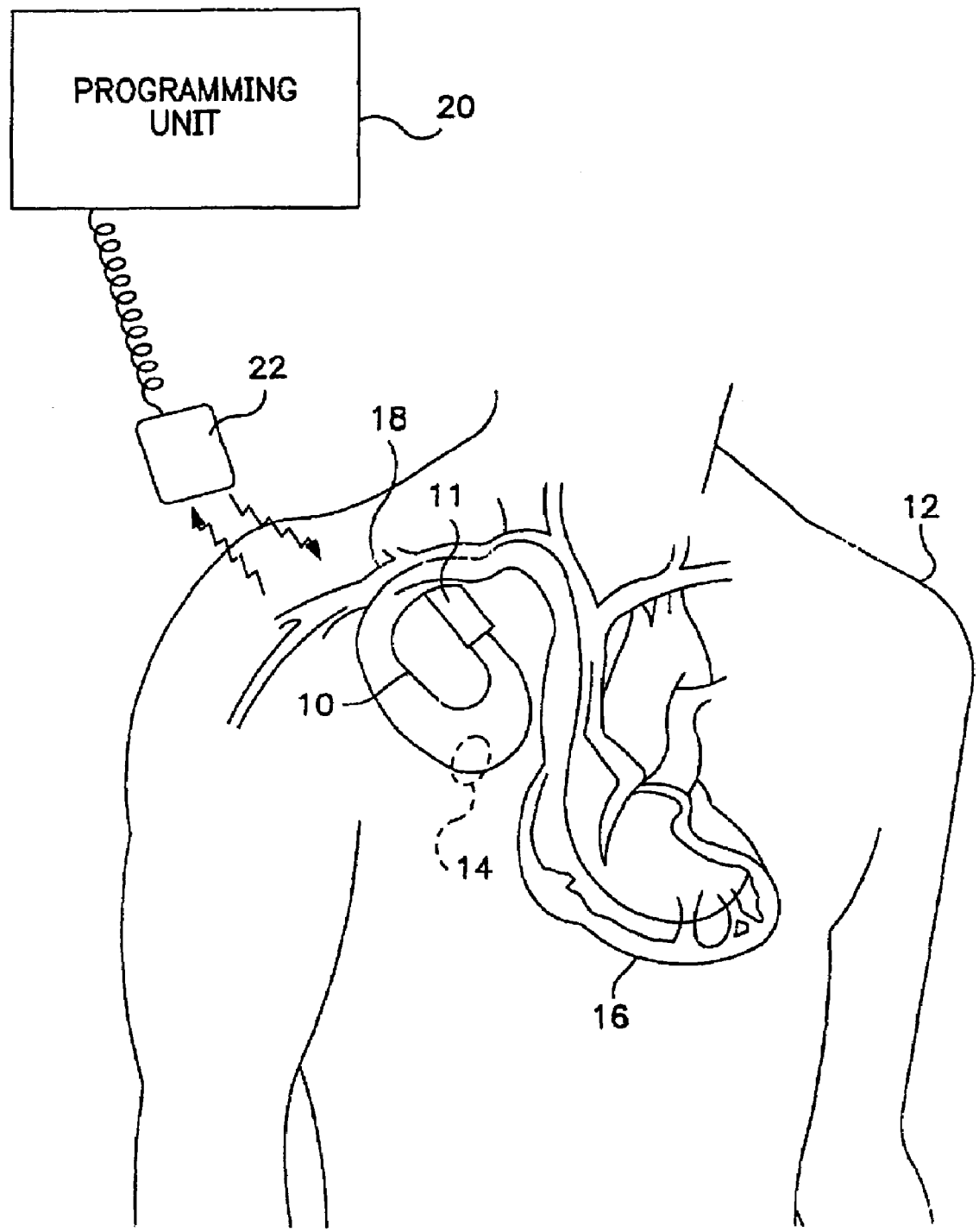
FIG. 1 is an illustration of a cardiac pacing system, including a hermetically sealed device implanted in a patient and an external programming unit, in accordance with an embodiment of the invention.

The following discussion is presented to enable a person skilled in the art to make and use the invention. Various modifications to the illustrated embodiments will be readily apparent to those skilled in the art, and the generic principles herein may be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the invention. Skilled artisans will recognize the examples provided herein have many useful alternatives which fall within the scope of the invention.

For purposes of illustration only, the invention is described below in the context of implantable cardiac pacemakers. However, embodiments of the invention are not limited to implantable cardiac pacemakers. Those of ordinary skill in the art having the benefit of the present teachings will appreciate that the invention may be practiced in connection with numerous other types of cardiac pacing devices and systems, and indeed in any application in which it is desirable to optimize the mechanical heart rate during coupled or paired pacing therapy, as may occur in implantable cardiac pacemakers, certain external/temporary cardiac pacing systems, dual-chamber implantable cardioverter defibrillators (ICDs), cardiac resynchronization therapy (CRT) devices, and similar devices and systems.

FIG. 1 is an illustration of an implantable medical device system adapted for use in accordance with the present invention. The medical device system shown in FIG. 1 includes an implantable device 10, a cardiac pacing device or pacemaker in this embodiment, that has been implanted in a patient 12. In accordance with conventional practice in the art, pacemaker 10 is housed within a hermetically sealed, biologically inert outer casing, which may itself be conductive so as to serve as an indifferent electrode in the pacemaker's or ICD's pacing/sensing/shocking circuit. One or more pacemaker leads, collectively identified with reference numeral 14 in FIG. 1, are electrically coupled to pacemaker 10 in a conventional manner via connector block 11 and extend into the patient's heart 16 via a vein 18. Disposed generally near the distal end of leads 14 are one or more exposed conductive electrodes for receiving (sensing) electrical cardiac signals and/or for delivering electrical pacing stimuli to heart 16. As will be appreciated by those of ordinary skill in the art, leads 14 may be implanted with distal ends situated in the atrium and/or ventricle of heart 16.

Also depicted in FIG. 1 is an external programming unit 20 for non-invasive communication with implanted device 10 via uplink and downlink communication channels, to be hereinafter described in further detail. Associated with programming unit 20 is a programming head 22, in accordance with conventional medical device programming systems, for facilitating two-way communication between implanted device 10 and programmer 20. In many known implantable device systems, a programming head such as that depicted in FIG. 1 is positioned on the patient's body over the implant site of the device (usually within 2- to 3-inches of skin contact), such that one or more antennae within the head can send RF signals to, and receive RF signals from, an antenna disposed within the hermetic enclosure of the implanted device or disposed within the connector block of the device, in accordance with common practice in the art.

Figure 2:
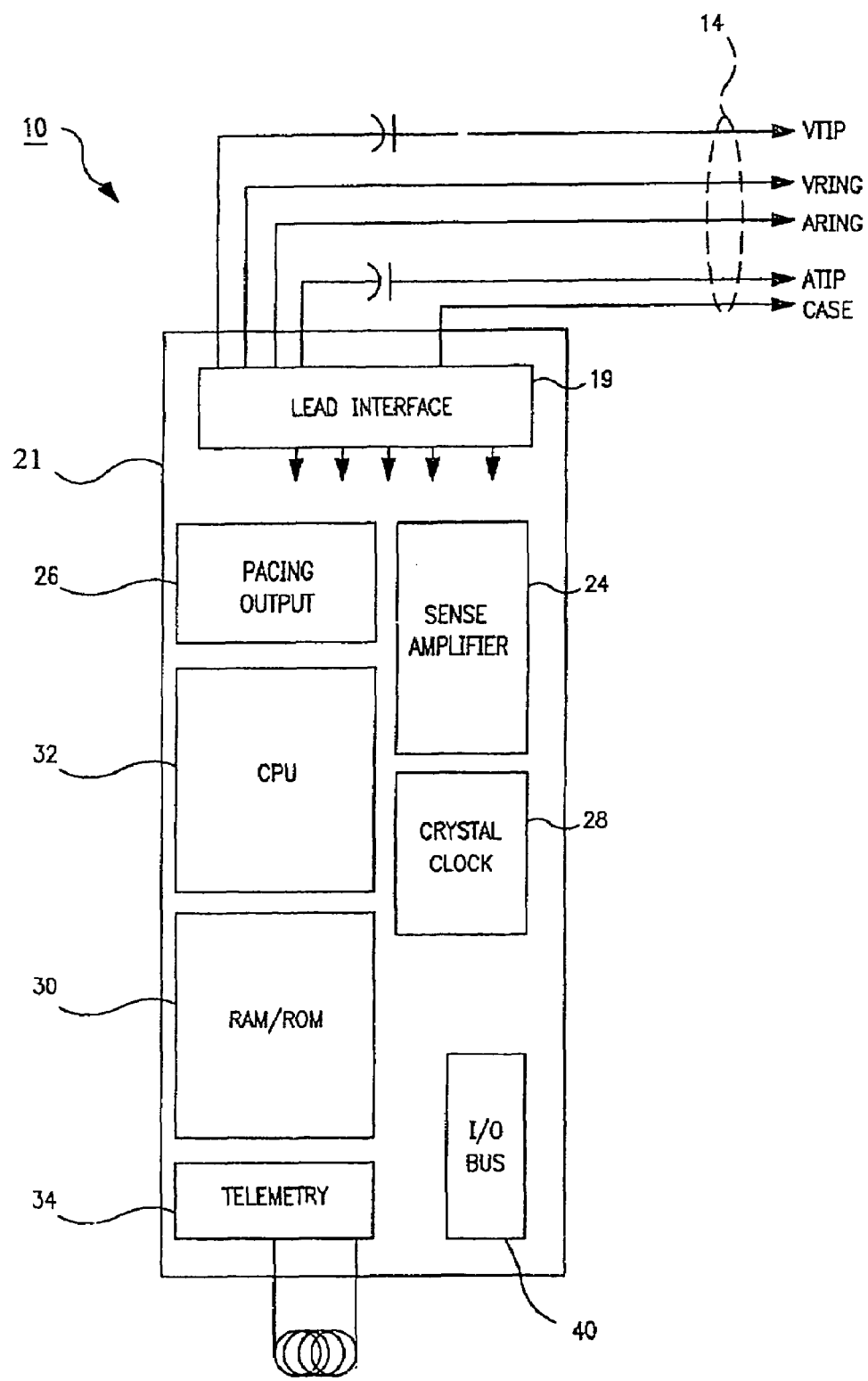
FIG. 2 is a block diagram of the implanted device from FIG. 1.

FIG. 2 is an exemplary block diagram of the electronic circuitry that makes up pacemaker 10 in accordance with certain embodiments of the invention. As can be seen from FIG. 2, pacemaker 10 comprises a primary stimulation control circuit 21 for controlling the device's pacing and sensing functions. The circuitry associated with stimulation control circuit 21 may be of conventional design, in accordance, for example, with what is disclosed U.S. Pat. No. 5,052,388 issued to Sivula et al., "Method and apparatus for implementing activity sensing in a pulse generator." To the extent that certain components of pacemaker 10 are conventional in their design and operation, such components will not be described herein in detail, as it is believed that design and implementation of such components would be a matter of routine to those of ordinary skill in the art. For example, stimulation control circuit 21 in FIG. 2 includes sense amplifier circuitry 24, stimulating pulse output circuitry 26, a crystal clock 28, a random-access memory and read-only memory (RAM/ROM) unit 30, and a central processing unit (CPU) 32, all of which are known in the art. Pacemaker 10 also includes internal communication circuit 34 so that it is capable of communicating with external programmer/control unit 20, described above.

With continued reference to FIG. 2, pacemaker 10 is coupled to one or more leads 14 which, when implanted, extend transvenously between the implant site of pacemaker 10 and the patient's heart 16, as previously noted with reference to FIG. 1. Physically, the connections between leads 14 and the various internal components of pacemaker 10 are facilitated by means of a conventional connector block assembly 11, shown in FIG. 1. Electrically, the coupling of the conductors of leads and internal electrical components of pacemaker 10 may be facilitated by means of a lead interface circuit 19 which functions, in a multiplexer-like manner, to selectively and dynamically establish necessary connections between various conductors in leads 14, including, for example, atrial tip and ring electrode conductors ATIP and ARING and ventricular tip and ring electrode conductors VTIP and VRING, and individual electrical components of pacemaker 10, as would be familiar to those of ordinary skill in the art. For the sake of clarity, the specific connections between leads 14 and the various components of pacemaker 10 are not shown in FIG. 2, although it will be clear to those of ordinary skill in the art that, for example, leads 14 will necessarily be coupled, either directly or indirectly, to sense amplifier circuitry 24 and stimulating pulse output circuit 26, in accordance with common practice, such that cardiac electrical signals may be conveyed to sensing circuitry 24, and such that stimulating pulses may be delivered to cardiac tissue, via leads 14. Also not shown in FIG. 2 is the protection circuitry commonly included in implanted devices to protect, for example, the sensing circuitry of the device from high voltage stimulating pulses.

As previously noted, stimulation control circuit 21 includes central processing unit 32 which may be an off-the-shelf programmable microprocessor or micro controller, but in the present invention is a custom integrated circuit. Although specific connections between CPU 32 and other components of stimulation control circuit 21 are not shown in FIG. 2, it will be apparent to those of ordinary skill in the art that CPU 32 functions to control the timed operation of stimulating pulse output circuit 26 and sense amplifier circuit 24 under control of programming stored in RAM/ROM unit 30. It is believed that those of ordinary skill in the art will be familiar with such an operative arrangement.

With continued reference to FIG. 2, crystal oscillator circuit 28 provides main timing clock signals to stimulation control circuit 21. The lines over which such clocking signals are provided to the various timed components of pacemaker 10 (e.g., microprocessor 32) are omitted from FIG. 2 for the sake of clarity. It is also to be understood that the various components of pacemaker 10 depicted in FIG. 2 are powered by means of a battery (not shown) that is contained within the hermetic enclosure of pacemaker 10, in accordance with common practice in the art. For the sake of clarity in the Figures, the battery and the connections between it and the other components of pacemaker 10 are not shown.

Stimulating pulse output circuit 26 functions to generate cardiac stimuli under control of signals issued by CPU 32. One of ordinary skill in the art may select from among various types of pacing output circuits that may be suitable. Sense amplifier circuit 24, which is of conventional design, functions to receive electrical cardiac signals from leads 14 and to process such signals to derive event signals reflecting the occurrence of specific cardiac electrical events, including atrial contractions (P-waves) and ventricular contractions (R-waves). Sense amplifier circuit 24 provides these event-indicating signals to CPU 32 for use in controlling the synchronous stimulating operations of pacemaker 10 in accordance with common practice in the art. In addition, these event-indicating signals may be communicated, via uplink transmission, to external programming unit 20 for visual display to a physician or clinician.

Pacemaker 10 may also include other components and subsystems, for example, activity sensors and associated circuitry not shown in FIG. 2.

Figure 3:
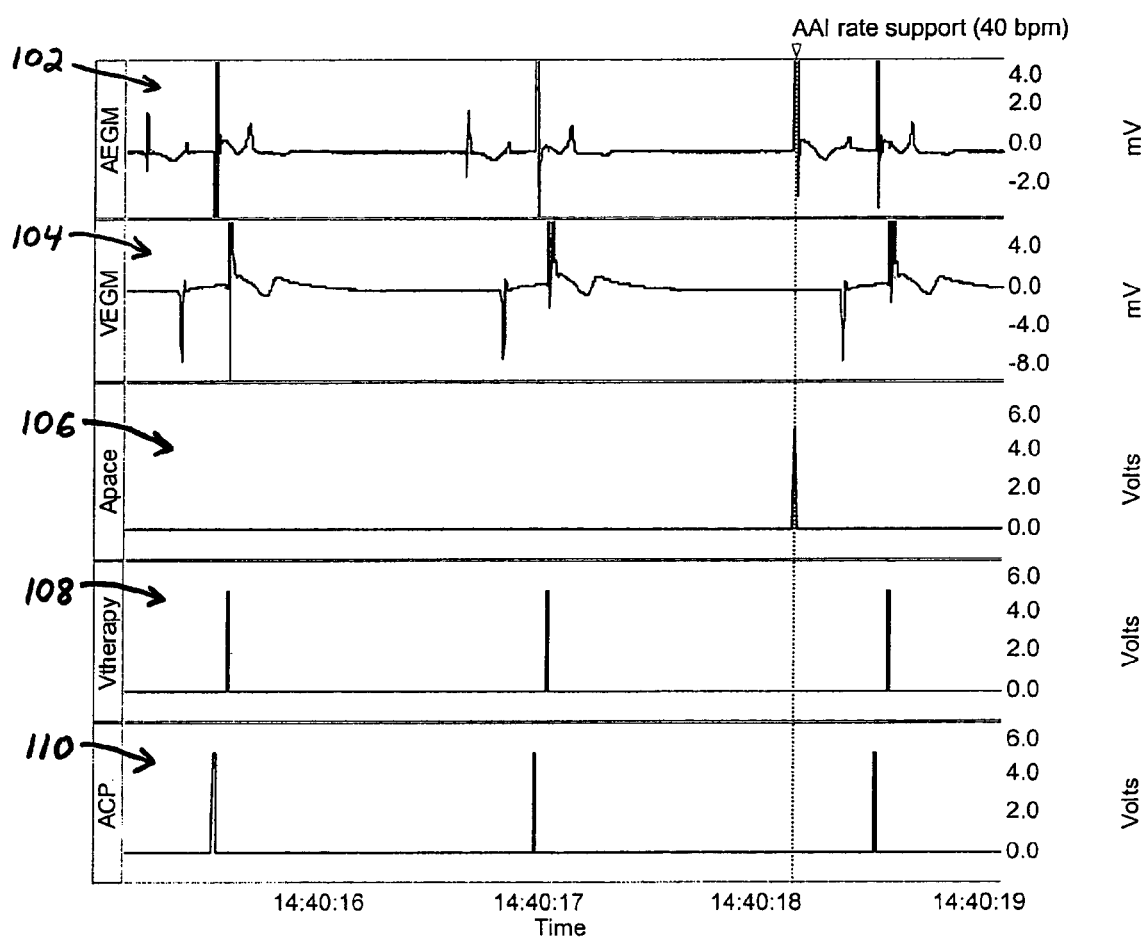
FIG. 3 is a timing diagram showing the use of a cardiac therapy in accordance with an embodiment of the invention.

FIG. 3 is a timing diagram showing an example of the use of ventricular PESP therapy in conjunction with atrial coordinated pacing (ACP). FIG. 3 shows (from top to bottom) an atrial electrogram (AEGM) signal 102, a ventricular electrogram (VEGM) signal 104, and timing signals that correspond to normal atrial pacing (Apace) 106, ventricular coupled (or paired) pacing (Vtherapy or Vth) 108, and ACP 110. The intended effect of this pacing regimen is to achieve a stable rhythm with enhanced mechanical function as a result of the PESP effect in both chambers. This pacing regimen may result in a lower mechanical rate due to the resetting of the sinus node by the atrial PESP pulse, but enhanced mechanical function may also result due to improved ventricular filling, intrinsic AV conduction, and natural ventricular depolarizations. In the example shown in FIG. 3, ventricular coupled pacing therapy 108 is shown being delivered after intrinsic ventricular depolarizations. In some embodiments, ventricular paired pacing (not shown) may be delivered after a ventricular pacing stimulus. FIG. 3 also illustrates that normal atrial pacing may occur when the sinus rate drops to an atrial pacing rate (40 bpm in the example of FIG. 3). It should be noted that the use of the term "mechanical rate" herein refers to the rate at which myocardial contractions of the atria or ventricles occur, rather than a rate derived from other criteria such as the Ap-Acp interval, for example.

FIGS. 4(a)-(d) illustrate timing relationships that may occur for a number of conditions relating to atrial and ventricular activity. Each timing diagram in FIGS. 4(a)-(d) shows atrial activity and therapy on the top portion of a timeline and ventricular activity and therapy on the bottom portion of the timeline. Information about the signals shown, such as amplitude or morphology, is not included to clarify the timing relationships illustrated. FIGS. 4(a)-(d) illustrate the timing of events that may be of interest to a cardiac pacing device in making therapy decisions, and may be considered analogous to information conveyed by marker channels used by cardiac pacing devices to present similar types of information.

Figure 4A:
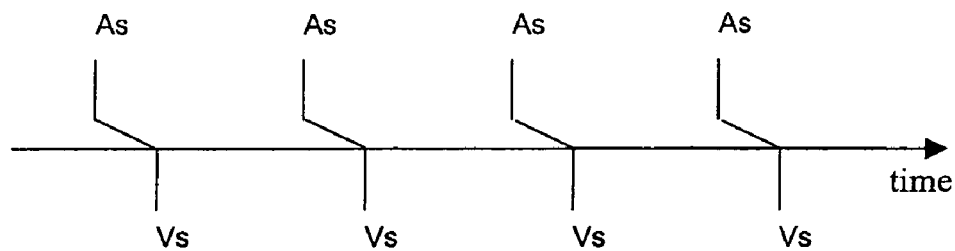
FIGS. 4(a)-(d) are a series of timing diagrams showing the effects of paired and coupled pacing.

FIG. 4(a) illustrates the timing relationships of atrial and ventricular sense events (As and Vs, respectively) for a heart in normal sinus rhythm. Each atrial instrinsic depolarization (denoted As for atrial sense event) conducts through the AV node to the ventricles and produces an intrinsic ventricular depolarization (denoted Vs for ventricular sense event). If the intrinsic atrial rate is too low, atrial pacing (not shown in FIG. 4(a)) may occur as a substitute for the atrial sense events shown.

Figure 4B:
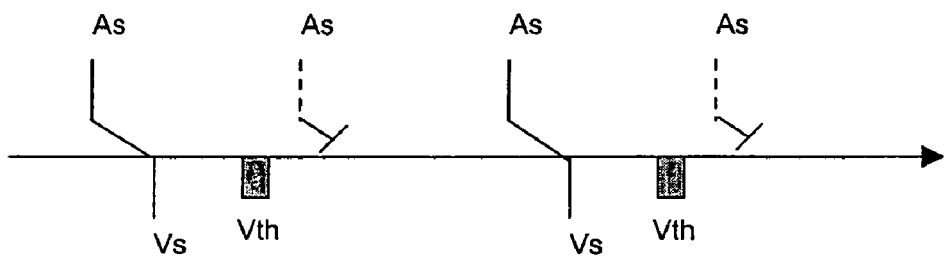

FIG. 4(b) illustrates the addition of ventricular stimulation therapy pulses (PESP therapy, denoted Vth) to the situation in FIG. 4(a). With the introduction of ventricular stimulation therapy, the ventricles become refractory a second time (after the Vth pulse) and a 2:1 conduction block pattern may arise in which every other atrial sense event is blocked from conducting to the ventricle. As a result, the mechanical rate of the ventricle is cut in half, as shown in FIG. 4(b). This pattern is sometimes unstable and may result in effective ventricular rates (mechanical rates) that are either too slow or too fast.

Figure 4C:
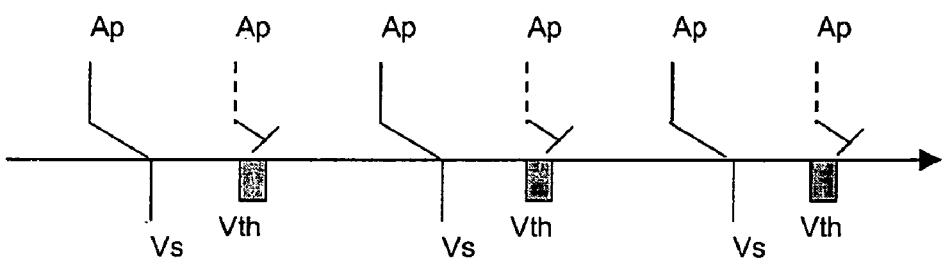

FIG. 4(c) illustrates a simple form of ACP in which the atria are paced (denoted Ap) at a rate faster than the intrinsic sinus rate; as a result, 2:1 conduction block is regularized. This approach may be helpful in situations such as in FIG. 4(b) above, where the result is an effective ventricular rate that may be too slow or too irregular. However, atrial pacing with regularized 2:1 block, as shown in FIG. 4(c), may prevent the subject's physiology from setting the mechanical heart rate, may pace the atrium too frequently, and may result in a heart rate that is too fast.

Figure 4D:
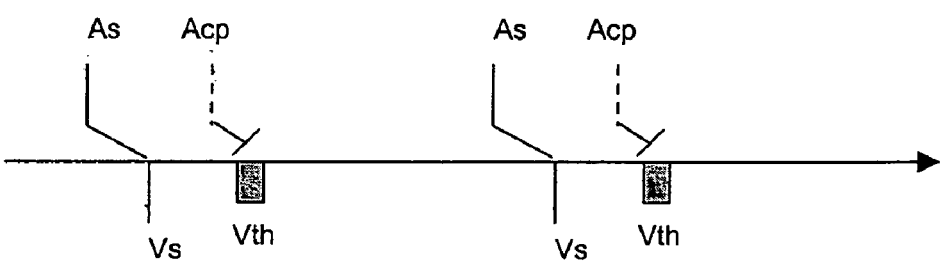

FIG. 4(d) shows an implementation of ACP in which the atria are paced for the purpose of coordination (denoted Acp) after the ventricular sense event and around the same time as the ventricular potentiation (Vth) pulse. The Acp pacing events result in resetting of the sinus node, but do not conduct to the ventricles (due to the refractoriness caused by the Vth pulse). The next atrial sense event therefore occurs at a time governed by physiologic demand. The potentiated beats are thus preceeded by adequate filling time, better coronary flow, and more time for myocyte ion fluxes to normalize.

It should be noted that the example shown in FIG. 4(d) illustrates coupled pacing stimuli being delivered in both chambers after a corresponding intrinsic depolarization. In other words, an atrial sense event (As) is followed by a coupled atrial pacing stimulus (Acp) at the end of an atrial extra stimulus interval (AESI), and a ventricular sense event is followed by a coupled ventricular pacing stimulus (Vth) at the end of a ventricular extra stimulus interval (VESI). Similarly, paired pacing stimuli may be delivered in one or both chambers after a corresponding paced stimulus. This may occur where the sinus rate and/or AV conduction have slowed below predetermined setpoints.

Normal atrial pacing may be employed in conjunction with ACP/PESP therapy, if the intrinsic atrial rate drops too low (as described in relation to FIG. 3 above), while maintaining the advantages of ACP/PESP just discussed. Furthermore, if AV or ventricular conduction is impaired, ventricular pacing at an appropriate AV (or VV) interval may also be employed in accordance with embodiments of the invention. For example, a minimum mechanical rate may be programmed to provide ventricular pacing at the end of a ventricular escape interval. Ventricular pacing may occur in the form of single site or multiple site (i.e., biventricular) pacing in certain embodiments of the invention. Pacing in the atrium or ventricle, when provided, may occur at rates that are programmable by an operator, and which may vary according to input sensor data, for example.

Figure 5:
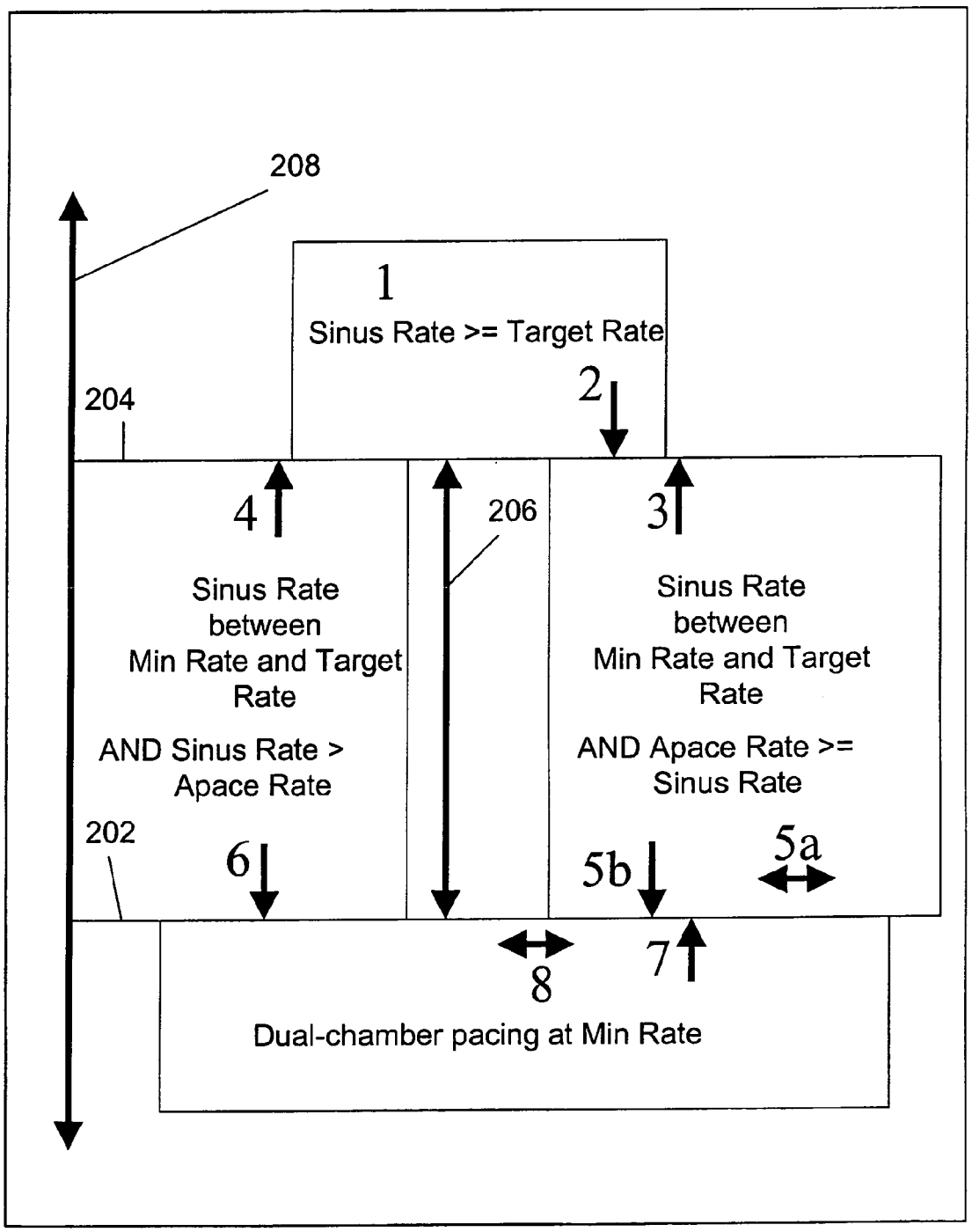
FIG. 5 is a chart of the various states of operation based on mechanical rate according to an embodiment of the invention.

FIGS. 5 and 6 describe a method of operating a pacemaker in accordance with an embodiment of the invention. FIG. 5 is a graphical illustration of how the mechanical heart rate is optimized by operating a cardiac pacing device with PESP according to an embodiment of the invention. FIG. 5 contains a plot of various possible "states" within which a cardiac pacing device may operate according to embodiments of the invention, determined by such physiological factors as sinus rate and the presence or absence of AV conduction, as well as by programmable pacing parameters, such as minimum mechanical rates and target pacing rates, for example. FIG. 6 provides a table of the states in which a cardiac pacing device may operate corresponding to the various states illustrated in FIG. 5. FIG. 6 also describes the action(s) the cardiac pacing device may take to achieve a desired outcome (i.e., to "transition" from one state to another, for example).

Certain aspects of the invention may be defined with continued reference to FIG. 5. The minimum mechanical rate ("Min Rate") 202 is a very slowly changing or static ventricular rate (also defined by its equivalent cycle length) at which ventricular pacing will occur in the absence of intrinsic ventricular contractions. In an embodiment of the invention, ventricular pacing at the Min Rate 202 may be delivered along with paired ventricular pacing (Vp-Vcp) in order to maintain the PESP effect in the ventricle and to ensure adequate systemic hemodynamics (arterial blood pressure and cardiac output). The Min Rate 202 may be a fixed rate, or may alternately be activity dependent, and may range from about 35-40 bpm at rest to about 40-50 bpm with exercise. Should the patient transiently experience AV block and become pacer dependent, the Min Rate parameter will serve as a safety net to provide back-up ventricular pacing.

Another rate parameter defined with reference to FIG. 5 is the target mechanical rate ("Target Rate") 204. The Target Rate 204 is also a very slowly changing (or static) rate parameter that may be met or exceeded by sinus node activity, or that may require atrial pacing to meet. This variable may be static, but may also be activity dependent in certain embodiments of the invention and may range from about 50-70 bpm at rest to about 60-90 bpm with exercise. In some embodiments of the invention, the Target Rate 204 may be determined using sensor input data from activity sensors and/or physiological sensors, as are known in the art.

The Min Rate 202 and the Target Rate 204 may be either static or slowly varying, as mentioned above, the Target Rate 204 being at least as large as the Min Rate 202. The variable rates may, for example, be computed from information derived from sensors to approximate appropriate rates associated with exercise or stress. Such information may be provided by a variety of sensors such as piezo-electric sensors, accelerometers, minute ventilation (i.e., trans-thoracic impedance) sensors, etc. The Min Rate 202 and Target Rate 204 may both be varied by such sensor inputs, or either rate alone may be so varied. The difference between the two rates is therefore not necessarily a constant value. For purposes of clarity, embodiments of the invention are described herein assuming that both the Min Rate 202 and Target Rate 204 are static values. One of ordinary skill in the art will readily appreciate that variable rates may be employed and are considered to be within the scope of the invention.

The Atrial paced Mechanical Rate ("Apace Rate") 206 is a variable atrial pacing rate that may be met or exceeded by sinus node activity. The Apace Rate 206 may be constrained by the Min Rate 202 and Target Rate 204 such that Min Rate≦Apace Rate≦Target Rate in certain embodiments of the invention. In certain embodiments of the invention, the Apace Rate 206 may be adjusted in response to such factors as the Target Rate, the actual mechanical heart rate, and the status of intrinsic AV conduction. For example, the Apace Rate 206 may be slowed to attempt to promote AV conduction, or may be raised to attempt to maintain a mechanical heart rate nearer the Target Rate 204.

The Intrinsic Sinus Mechanical Rate ("Sinus Rate") 208 is the current ventricular mechanical rate during therapy delivery that is, or that could be, obtained by tracking the intrinsic sinus rate (i.e. As-As). If atrial pacing is currently occurring, the Sinus Rate 208 is known to be less than the Apace Rate 206 (since sinus activity above the Apace Rate 206 will cause atrial pacing to be inhibited). The Sinus Rate 208 is a physiologically determined rate and is an instantaneous function of factors such as physical activity, the effect of the sinus node being reset by the ACP therapy, and possibly the immediate past history of systemic hemodynamics and rate. Various embodiments of the invention may provide PESP therapy at the Sinus Rate 208.

It should be noted that paired pacing may not be desired in all patients. The PESP therapy may be suspended in certain embodiments of the invention should the mechanical rate (or other rate-related hemodynamic indices) or AV conduction slows enough to require paired pacing in patients where the arrhythmia risk is considered too high. Such a modification to the therapy may be applied to either the atria or ventricles or to both chambers in some embodiments of the invention.

The Actual Mechanical Rate ("Actual Rate" or "Mechanical Rate") is the current ventricular mechanical rate during therapy delivery. The Actual Rate equals the maximum of the Sinus Rate and the Apace Rate. The Actual Rate may vary as a function of patient physiology according to certain embodiments of the invention, as well as with changes in programmed settings such as the Min Rate and Target Rate 202, 204. In some embodiments of the invention, the PESP therapy adjusts pacing parameters to attempt to achieve an Actual Rate equal to the Target Rate 204. The Actual Rate may be higher than the Target Rate 204, for example when the Sinus Rate 208 is above the Target Rate 204. However, the Actual Rate should not fall below the Min Rate 202, so long as ventricular pacing is provided at the Min Rate 202 as a safety net.

There are 9 states of operation that may be defined with reference to FIG. 5. These states are numbered 1-9 in FIG. 5, and are further defined in the table of FIG. 6. The state of operation is determined by 3 criteria: 1) the Actual Rate (relative to the Target Rate and Min Rate), 2) whether Atrial Pacing or Sinus Rate is greater, and 3) whether AV conduction block is present.

Reference may also be made to FIGS. 5 and 6 to describe the actions taken at each state, and the possible transitions between the various states. For example, a heart that has a Sinus Rate 208 that is above the Target Rate 204, and in which there is no AV conduction block, may be considered to be operating in the top region of FIG. 5 at the point labeled 1, corresponding to State 1 in FIG. 6. In state 1, PESP therapy is delivered to both chambers at a physiologically chosen rate in the form of coupled pacing following intrinsic atrial and ventricular sense events (As-Acp, and Vs-Vcp), as shown in FIG. 4(*d*).

From State 1, the patient may experience instances of AV conduction block. AV conduction block may, for example, be defined as the absence of a ventricular sense event (Vs) occurring within some predefined interval after an atrial event (As or Ap), or as an increase in the A-Vs interval beyond some predetermined interval (i.e., 400 msec). In some embodiments of the invention, the presence or absence of AV conduction may be "detected" by an analysis of AV conduction block over a plurality of cardiac cycles. For example, if AV conduction block occurs in 6 of the last 8 cardiac cycles, then the absence of AV conduction is detected and the state will change. From State 1, detecting the absence of AV conduction will result in the state changing to State 2, as described in FIGS. 5 and 6. In one embodiment, the presence of AV conduction may be defined to exist at any time that the absence of AV conduction is not detected, for example. Alternately, in some embodiments of the invention, a separate criterion may be employed to again detect the presence of AV conduction after first detecting its absence, for example, requiring that no AV conduction block occur for 3 of the last 4 cardiac cycles. As will be apparent to one of ordinary skill in the art, a number of means for detecting the presence or absence of AV conduction may be devised for use in accordance with embodiments of the invention and are considered to be within the scope of the invention.

In an embodiment of the invention, the cardiac pacing device 10 may respond to State 2 by increasing the atrial extra stimulus interval (AESI, or As-Acp interval). Increasing the AESI attempts to restore intrinsic AV conduction by slowing the sinus rate. The sinus rate is slowed by delaying the occurrence of the atrial coupled stimulus for a longer period of time after the atrial sense event, thereby interrupting ("resetting") the sinus node at a later point in time in the cardiac cycle.

State 3 in FIGS. 5 and 6 occurs when the Actual Rate is an Atrial Pacing Rate (i.e., the Atrial Pacing Rate is greater than the Sinus Rate) that is at or below the Target Rate, and when no AV block occurs. State 3 may be reached in a variety of ways, such as from State 1, by a physiological slowing of the sinus rate for example, or from State 2, by the intended result of extending the AESI described above. (State 3 may also be reached from other states illustrated in FIG. 5; this will be discussed separately below.) At State 3, the Sinus Rate has decreased to a level at or below the Target Rate. At this point, atrial pacing should occur at the Atrial Pacing Rate. In some embodiments, the Atrial Pacing Rate will be the same as the Target Rate as the rate slows, for example from State 2, and atrial pacing will begin at the Target Rate. However, in some embodiments, it may be desirable to have an "offset" between the Atrial Pacing Rate and the Target Rate (for example 5-10 bpm) such that the Sinus Rate is allowed to decrease to a certain level below the Target Rate before atrial pacing is initiated.

When the Atrial Pacing Rate is below the Target Rate, the response at State 3 is to periodically increase the atrial pacing rate (by decreasing the atrial escape interval) to attempt to raise it back to the Target Rate. This "probing" may be done at a predetermined number of cardiac cycles, for example, and is done while attempting to maintain AV conduction. In other words, if AV conduction is maintained, the Atrial Pacing Rate will be successively increased until it reaches the Target Rate. If AV conduction is lost during a probing attempt, the result is a change to State 5.

At State 3, atrial pacing at the Atrial Pacing Rate may be accompanied by AV conduction block. If the AV conduction block condition results in detection of the absence of AV conduction, this results in a change to State 5 as described in FIGS. 5 and 6. The response in State 5 is first to attempt to restore AV conduction by decreasing the AESI (the Ap-Acp interval). This is shown in FIGS. 5 and 6 as State 5a. This action effectively increases the amount of time between the Acp and the following Ap (since the Apace Rate has not yet changed), allowing more time for the AV node to recover, thereby encouraging AV conduction.

In the event that decreasing the Ap-Acp interval does not result in AV conduction, the method next attempts to restore AV conduction by slowing the Apace Rate, as indicated by State 5b in FIGS. 5 and 6. State 5b involves lengthening the Ap-Ap interval, which results in a lower Apace Rate. The lower paced atrial rate is intended to allow more time for the AV node to recover and thereby encourages intrinsic AV conduction. State 5b may result in lowering the Apace Rate all the way down to the Min Rate. At the Min Rate, if there is still AV block (i.e., the absence of AV conduction is detected), State 8 may occur, resulting in a switch to a dual-chamber pacing mode at the Min Rate (i.e., DDI/R mode, Ap-Ap interval at the Min Rate and Vp-Vp interval at the Min Rate). As previously noted, PESP therapy may be continued in both chambers, although this may involve paired pacing in the ventricle with the attendant risk of arrhythmia induction. In one embodiment of the invention, PESP may be disabled in one or both chambers if ventricular pacing is required.

As noted above, State 8 results in a switch to a dual-chamber pacing mode at the Min Rate. From State 8, periodic attempts may be made to restore AV conduction. For example, State 8 employs an attempt to restore AV conduction by periodically inhibiting ventricular pacing to "probe" for the presence of AV conduction. If AV conduction is restored by this effort, a state change to State 7 results. Similarly, if the presence of AV conduction is detected while at State 8 (i.e., AV conduction spontaneously returns), a state change to State 7 results.

In State 7, the method periodically attempts to raise the Apace Rate above the Min Rate by decreasing the Ap-Ap interval. "Probing" in this manner is done to determine if AV conduction can be sustained at a higher Apace Rate. The actions taken in States 7 and 8, when successful, bring the condition back up to State 3.

In certain instances, the patient's Sinus Rate may, on its own, exceed the Apace Rate while between the Min Rate and the Target Rate. For example, if the Sinus Rate increases above the Apace Rate while in State 3 (but is still below the Target Rate), and if there continues to be no AV conduction block, this results in State 4. State 4 is similar to State 1 (coupled pacing in both chambers), but at a rate below the Target Rate. State 4 attempts to raise the Actual Rate toward the Target Rate by decreasing the Ap-Ap interval. This effectively puts the condition back in State 3 as soon as the Apace Rate exceeds the Sinus Rate, and the device will continue to try to raise the Actual Rate back up to the Target Rate as long as there is intact AV conduction. If AV block occurs while in State 4, this results in State 6. State 6 is similar to State 2 except that the Sinus Rate is below the Target Rate. State 6 therefore employs the same response as State 2, increasing the As-Acp interval to slow down the Sinus Rate and thereby promote AV conduction. State 6 may result in bringing the Actual Rate all the way down to State 8 if the Sinus Rate decreases below the Min Rate and AV block persists, for example.

Thus, embodiments of the METHOD OF OPTIMIZING MECHANICAL HEART RATE DURING DELIVERY OF DUAL-CHAMBER COUPLED OR PAIRED PACING are disclosed. One skilled in the art will appreciate that the present invention can be practiced with embodiments other than those disclosed. The disclosed embodiments are presented for purposes of illustration and not limitation, and the present invention is limited only by the claims that follow.

The invention claimed is:

1. A method of operating a cardiac pacing device during coupled or paired pacing comprising:

implementing an atrial-based pacing mode comprising sensing intrinsic atrial depolarizations and generating an atrial sense event signal in response thereto;

providing atrial pacing pulses to the atrium of the heart at an atrial pacing rate, each atrial pacing pulse separated by an atrial escape interval corresponding to the atrial pacing rate, and restarting the atrial escape interval in response to an atrial sense event signal;

sensing intrinsic ventricular depolarizations and generating a ventricular sense event signal in response thereto; and detecting the presence or absence of AV conduction;

providing paired or coupled pacing pulses in the atrium at an atrial extra stimulus interval (AESI) timed from immediately preceding atrial pacing pulses and atrial sense event signals, respectively, sufficient to effect post-extra-systolic potentiation (PESP) of the atrium; and adjusting the AESI when the absence of AV conduction is detected to attempt to restore AV conduction.

2. The method of claim 1 wherein the step of detecting the presence or absence of AV conduction further comprises analyzing AV conduction block over a plurality of cardiac cycles.

3. The method of claim 1 further comprising:
providing coupled pacing pulses in the ventricle at a ventricular extra stimulus interval (VESI) timed from immediately preceding ventricular sense event signals, sufficient to effect PESP of the ventricle.

4. The method of claim 1 further comprising:
adjusting the atrial escape interval when the presence of AV conduction is detected and when the atrial pacing rate is below a target pacing rate to attempt to move the atrial pacing rate toward the target pacing rate.

5. The method of claim 4 wherein the step of adjusting the atrial escape interval includes decreasing the atrial escape interval to move the atrial pacing rate toward the target pacing rate.

6. The method of claim 4 wherein the target pacing rate is a variable rate setting calculated from input sensor data.

7. The method of claim 1 further comprising:
switching to a dual-chamber pacing mode to provide ventricular pacing pulses to the ventricle of the heart at a minimum mechanical rate, each ventricular pacing pulse separated by a ventricular escape interval corresponding to the minimum mechanical rate, and restarting the ventricular escape interval in response to a ventricular sense event signal.

8. The method of claim 7 further comprising:
switching back to the atrial-based pacing mode in response to a ventricular sense event signal.

9. The method of claim 7 further comprising:
while in the dual-chamber pacing mode, providing paired pacing pulses in the ventricle at a ventricular extra stimulus interval (VESI) timed from the immediately preceding ventricular pacing pulses, sufficient to effect post-extra-systolic potentiation of the ventricle.

10. The method of claim 7 further comprising:
while in the dual-chamber pacing mode, periodically inhibiting ventricular pacing to attempt to restore AV conduction.

11. The method of claim 10 further comprising:
periodically decreasing the atrial escape interval to attempt to move the atrial pacing rate toward the target pacing rate.

12. The method of claim 7 wherein the minimum mechanical rate is a variable rate setting calculated from input sensor data.

13. The method of claim 1 wherein the step of adjusting the AESI and includes increasing the AESI after an atrial sense event.

14. The method of claim 1 wherein the step of adjusting the AESI includes decreasing the AESI after an atrial pacing pulse.

* * * * *

UNITED STATES PATENT AND TRADEMARK OFFICE
CERTIFICATE OF CORRECTION

PATENT NO. : 7,286,873 B2  Page 1 of 1
APPLICATION NO. : 11/096388
DATED : October 23, 2007
INVENTOR(S) : William Havel et al.

It is certified that error appears in the above-identified patent and that said Letters Patent is hereby corrected as shown below:

Col. 16, line 32, delete "AESI and includes" and insert in place there of --AESI includes--.

Signed and Sealed this

Sixth Day of January, 2009

JON W. DUDAS
*Director of the United States Patent and Trademark Office*